| United States Patent [19]
Lau

[11] Patent Number: 4,705,687
[45] Date of Patent: Nov. 10, 1987

[54] TREATMENT OF AUTOIMMUNE DISEASES SUCH AS RHEUMATOID ARTHRITIS WITH SUPPRESSOR FACTOR

[75] Inventor: Catherine Y. Lau, Unionville, Canada

[73] Assignee: Ortho Pharmaceutical (Canada) Ltd., Canada

[21] Appl. No.: 745,116

[22] Filed: Jun. 17, 1985

[51] Int. Cl.$^4$ ............................................. A61K 35/12
[52] U.S. Cl. ...................................... 424/95; 514/885
[58] Field of Search .......................... 424/95; 514/885

[56] References Cited

U.S. PATENT DOCUMENTS 4,239,498 12/1980 Rule ....................................... 424/88
4,364,935 12/1982 Kung et al. ............................ 424/85

FOREIGN PATENT DOCUMENTS 0127394 5/1984 European Pat. Off. .............. 435/68

OTHER PUBLICATIONS

"Graft-Versus-Host Disease in Murine Bone Marrow . . .", Gorczynski et al., Immun. Ltrs. 11 (1985) 293–299.
"Purification and Characterization of a Suppressor Activating Factor", C. Lau et al., Abstracts, 6th Int'l Congress of Immun., Jul. 6–11, 1986, Toronto, Canada, No. 3.53.6.
"Suppressor-Activating Factor (SAF) Does Not Inhibit Interleukin 2 (IL 2) Receptor . . . ", Messino et al., Abstracts, 6th Int'l Congress of Immun., Jul. 6–11, 1986, Toronto, Canada, No. 6.13.21.
"Impaired Release of a T-cell Specific Suppressor Factor in Rheumatoid Arthritis", Lau et al., Clin. exp. Immunol. (1985) 61, 489–495.
"Treatment of Active Rheumatoid Arthritis with Slow . . . ", Malaise et al., The Lancet, Apr. 13, 1985, pp. 832–836.
"Effect of Thymopoietin Pentapeptide (TP5) on Autoimmunity", *The Journal of Immunology*, vol. 125, No. 4, Oct. 1980, pp. 1634–1638.
*Nature, New Biology*, "Induction of Red Cell Autoantibodies in Normal Mice", vol. 243, No. 128, Jun. 13, 1973, pp. 213–214.
*Nature*, "Suppressor T Cells in Experimental Autoimmune Haemolytic Anaemia", vol. 273, May 11, 1978, pp. 154–155.
Chem. Abst., 101:70779p, 1984.
Lau et al., J. Imm. 134(5):3155–3162, 1985.

*Primary Examiner*—Johnnie R. Brown
*Assistant Examiner*—John W. Rollins, Jr.

[57] ABSTRACT

Method of treating autoimmune diseases such as rheumatoid arthritis by administration of a suppressor factor obtained in the supernatant of a human cell line. A particular human cell line is CEM which has survived treatment with 6-thioguanine.

20 Claims, No Drawings

TREATMENT OF AUTOIMMUNE DISEASES SUCH AS RHEUMATOID ARTHRITIS WITH SUPPRESSOR FACTOR

BACKGROUND OF THE INVENTION

The mammalian immune system includes a complex array of organs, cells and soluble products of cells. Organs involved in the immune system include the bone marrow, spleen and lymph nodes; a wide variety of cells populate the immune system and this includes macrophages, granulocytes and T and B lymphocytes. Examples of soluble products produced by immune system cells include antibodies (produced by B lymphocytes) and lymphokines (produced by T-lymphocytes). The latter play an important role in regulating the immune system.

The basic functions of the immune system include:
(a) identification of substances or cells within the body to determine whether they are "self" or "non-self".
(b) communication between cells to facilitate a response to "non-self" entities.
(c) specific action on "non-self" substances or cells, for example specific lysis (dissolution) of a foreign cell.

The immune system is responsible for manifestations which include destruction of infecting organisms and the antoimmune reaction which is thought to be a malfunction of the system. It is now recognized that for various reasons and in view of various factors including aging, genetic makeup of the individual, viruses, thymic defects and hormones, the mammalian body may produce antibodies against parts of itself resulting in autoimmune diseases which include myasthenia gravis, autoimmune hemolytic anemia and rheumatoid arthritis.

Medical treatment of rheumatoid arthritis consists of the administration of drugs which may be classified as steroids, non-steroidal anti-inflammatory agents, gold salts and immuno-suppressive agents. Corticosteroids are used with caution, however, in view of serious side effects associated with long term use, including degenerative arthritis, hyperadrenocorticism and disruption of the pituitary-adrenal axis. Non-steroidal anti-inflammatory drugs such as aspirin, fenoprofen, ibuprofen and tolmetin are useful in long-term therapy provided that the side effects of high dosage, e.g. tinnitus, gastric upset and a decrease in platelet adhesiveness, are tolerated. Gold salts are associated with a high incidence of toxic side effects including dermatitis and aplastic anemia. Dramatic improvements in rheumatoid arthritis have been seen with immunosuppressive agents such as chlorambucil, cyclophosphamide, mercaptopurine and azathioprine. However, such drugs are associated with serious toxicity, may be teratogenic and may cause increases in lymphoma and infection. For these reasons, the routine use of immunosuppressive agents has been discouraged, see Chapter 26 entitled "Rheumatic Diseases" by K. H. Fye and K. E. Sack in the text "Basic and Clinical Immunology" by D. P. Stites et al. Lange Medical Publications, Los Altos, Calif. 94022 (1982).

It is an object of the present invention to provide an immunosuppressive therapy for mammals such as man afflicted with an autoimmune disease such as rheumatoid arthritis. A further object is a therapy which has few side effects and does not seriously affect the patient's ability to combat non-self antigents, e.g. infection.

SUMMARY OF THE INVENTION

The invention comprises a method for the treatment of autoimmune diseases such as rheumatoid arthritis by the administration of a factor which may be derived from the human acute lymphoblastic leukemic cell line CEM. The particular cell line is obtained by culturing the CEM line with 6-thioquanine and recovering the small percentage of cells which survive, i.e. the 6-T resistant cells. The supernatant factor used in the present invention from the thus-produced cultured 6-T CEM cells is designated the "suppressor activating factor" or "SAF". SAF has been found to suppress production of autoantibodies in test animals immunized with cross-reacting antigenic materials compared to control animals immunized with the antigenic materials and treated with control vehicle alone.

The following abbreviations may be used in the present specification:
AIHA=autoimmune hemolytic anemia
ATCC=American Type Culture Collection
CEM=the lymphoblastic leukemic cell line CCRF-CEM (ATCC CCL 119)
DAIT=direct anti-immunoglobulin test
FCS=fetal calf serum
α-MEM=minimum essential medium
N=normal
PBS=phosphate buffered saline
RBC=red blood cells
SAF=suppressor activating factor
6-T=6-thioquanine

DETAILED DESCRIPTION OF THE INVENTION

The method of the present invention comprises the treatment of a mammal having an autoimmune disease by the administration of a suppressor activating factor. In particular, the method is applicable to the treatment of humans.

Autoimmunity can be defined as a state in which immune mechanisms are directed against "self" as opposed to "non-self". Autoimmune disease can be defined as the pathlogical consequence of certain "self" directed immune mechanisms. Autoimmunity is relevant to many applications involving several different organ systems. Further, autoimmune diseases may be classified systemic or organ-specific. Examples of systemic autoimmune diseases include Goodpasture's syndrome, rheumatoid arthritis, Siogren's syndrome and systemic lupus erythematosus. Examples of organ-specific autoimmune diseases include myasthenia gravis, Graves' disease (diffuse toxic goiter), multiple sclerosis, Hashimoto's thyroiditis, insulin-resistant diabetes associated with acanthosis nigricans, insulin-resistant diabetes associated with ataxia-telangiectasia, allergic rhinitis asthma, functional autonomic abnormalities, juvenile insulin-dependent diabetes. Pernicious anemia, Addison's disease, idiopathic hypoparathyroidism, spontaneous infertility, premature ovarian failure, pemphigus, bullous pemphigoid, primary biliary cirrhosis, autoimmune hemolytic anemia, idiopathic thrombocytopenic purpura and idiopathic neutropenia.

The method of the present invention is applicable in particular to rheumatoid arthritis and autoimmune hemolytic anemia as explained below.

Rheumatoid Arthritis

Short et al. in "Rheumatoid Arthritis", Harvard Univ. Press, Cambridge, Mass. (1957) have defined rheumatoid arthritis as a chronic inflammatory disorder of unknown etiology which is systemic in nature and is characterized by the manner in which it involves joints. Both cellular and humoral immunological events mediate its pathogenesis; for example, lymphokines and large numbers of T-cells are frequently found in synovial tissues and fluids and many pieces of evidence link altered T-cell function with disease activity in rheumatoid arthritis: see the articles "Lymphocyte subsets and inflammatory indices in synovial fluid and blood of patients with rheumatoid arthritis" by J. V. Bertouch in *J. Rheumatol* (1984): 11:754–9; "Rheumatoid arthritis: a disease of T-lymphocyte-macrophage immunoregulation" by G. Janossy in *Lancet* (1981): 2:839–42; and "In situ localization of lymphocyte subsets in synovial membranes of patients with rheumatoid arthritis with monoclonal antibodies", by C. J. L. M. Meijer in *J. Rheumatol.* (1982): 9:359–65. Alterations in in vitro characteristics of T lymphocytes from rheumatoid arthritis patients have been reported to correlate with altered cellular interactions and activity of the disease, as described by R. M. Pope in "Arthritis and Rheumatism" (1984): 24:1234–44.

Thus, therapies directed towards the normalization of T lymphocyte function in rheumatoid arthritis may well be beneficial in its treatment. To this end, many broadly-active immunosuppressive agents have been tested in experimental autoimmune disease models, e.g. cyclophosphamide and betamethazone. Based on these encouraging animal data, immunosuppressive agents have been introduced into clinical medicine for the treatment of a number of autoimmune diseases including rheumatoid arthritis. Despite their clinical efficacy, however, these drugs have only limited utility in therapeutic medicine due to their propensity to cause toxicity during long-term administration as a result of their broad, non-specific immunosuppressive action.

Autoimmune Hemolytic Anemia

Hemolytic anemia is a condition in which lysis or destruction of erythrocytes is a diagnostic feature. In almost all cases of acquired hemolytic anemia in which no cause is found and no associated disease recognized, autoimmune mechanisms appear to be the root of the problem, see M. M. Wintrobe in "Clinical Hematolgoy", 6th ed., p. 626, Lea and Febiger, Philadelphia (1967). Several animals models have been developed which mimic certain aspects of human autoimmune hemolytic anemia.

The suppressor activating factor (SAF) used in the method of the present invention:

(i) is secreted by a stable 6-thioguanine-resistant mutant of the lymphoblastoid cell line CEM.
(ii) is non-mitogenic, and
(iii) is non-cytotoxic.

In more detail, the SAF used in the method of the invention:

(iv) suppresses at least 90% of mitogen-induced T cell proliferation at a dilution of $10^{-6}$ but does not suppress mitogen-induced B cell proliferation at said dilution.
(v) is contained in a high molecular weight protein, e.g. of about 110,000 dalton.
(vi) exhibits maximum suppressor activity at physiological pH.
(vii) is inactivated at 56° C.
(viii) suppresses mouse spleen cell proliferation to mitogenic stimulation with the same potency as it suppresses human peripheral blood lymphocyte proliferation to mitogenic stimulation.
(ix) exhibits a greater suppressive effect on autoantibody production than an antibody production directed at foreign antigens (rat erythrocytes) in mice immunized with said rat erythrocytes.

The SAF may be obtained from the supernatant produced by those cells of the CEM lymphoblastic leukemic cell line which are resistant to destruction by 6-thioguanine as described in the following preparations A, B, C and D and in my co-pending U.S. patent application Ser. No. 586,515 filed Mar. 5, 1984 which is a continuation-in-part of my U.S. patent application Ser. Nos. 495,908 filed May 18, 1983 and 534,526 filed Sept. 21, 1983. U.S. Ser. Nos. 495,908 and 534,526 are now abandoned. European patent application ("EPO") No. 127,394 published Dec. 5, 1984 is the equivalent of my U.S. Ser. No. 586,515 and is incorporated by reference in the present specification for the preparation of SAF, designated therein as SIF or suppressor-inducer factor.

A. Generation of 6-thioquanine (6T) resistant mutant 6T-CEM and the subclone 6T-CEM-20

The 6-thioquanine (2-amino-6-mercaptopurine: 6T) was obtained from Sigma (Cat. No. A-4882). 100 mg of 6T was dissolved in 100 ml of distilled water. 1 or 2 drops of 10N NaOH were added to help the 6T to dissolve completely. The pH of the final solution is about 9.

The lymphoblastic leukemic line CEM (CCRF-CEM, ATCC CCL 119) was obtained from the American Type Culture Collection, Rockville MD, and was maintained in 90% α-MEM and 10% FCS. CEM cells at log phase ($10^6$ cells/well) were treated with various concentrations of 6T and viability was assayed 7 days later as shown in the following Table 1:

TABLE 1

| 6-Thioguanine (μg/ml) | % Cell Viability[1] |
|---|---|
| 0.5 | 51 |
| 5 | 43 |
| 10 | 32 |
| 20 | 5 |
| 30 | 4 |

[1]CEM cells were exposed to various concentrations of 6T for 7 days and viability was assayed by dye exclusion.

Cells treated with 30 μg/ml of 6T were selected for further studies. The remaining viable cells (4%) were grown in 25 mm culture flasks until a significant number of cells was observed, after which dead cells were removed by a Ficoll-Hypaque gradient. The viable cells were divided into 2 parts. One part was maintained in α-MEM+FCS with fresh medium added every third day and the cells were passaged every week. The other part was plated in 96 well microtitre plates for subcloning. The subclones grew up in about 2-3 weeks, after which they were transferred to 24 well Linbro trays. When the cells reached a density of $10^6$/well, they were tested for aminopterin sensitivity and production of SAF as shown in the following Table 2:

TABLE 2

| Cell Lines | % Viability[1] | Suppressor[2] Activity |
|---|---|---|
| CEM | 100 | $5 \times 10^{-3}$ |
| 6T-CEM | 10 | $10^{-6}$ |
| 6T-CEM 2 | 0 | $10^{-6}$ |
| 4 | 0 | $10^{-6}$ |
| 13 | 2 | $>10^{-6}$ |
| 14 | 4 | $10^{-6}$ |
| 17 | 2 | $>10^{-6}$ |
| 18 | 0 | $10^{-6}$ |
| 19 | 0 | $10^{-6}$ |
| 20 | 1 | $10^{-9}$ |

[1]CEM, 6T-CEM and it subclones were tested for their sensitivity to aminopterin treatment (0.005 μg to 0.5 μg/ml). The viabilities of various cell lines after 7 day exposure to 0.05 μg of aminopterin were shown.
[2]Suppressor effect of T-Cell proliferation was measured according to the method described in Example IV of my EPO 127,394 published December 5, 1984. The dilutions of various supernatants exhibiting 50% suppression was shown. The entry ">$10^{-6}$" means that 50% suppression was attained at dilutions higher than $10^{-6}$.

6T-CEM-20, one of the subclones which showed the highest level of SAF production, was selected for further studies. The line 6T-CEM-20 has been showing a consistent level of SAF secretion for greater than three years, indicating no loss of chromosome(s) involved in the secretion of the factor. The growth characteristics, karotype, sensitivity to aminopterin, level of suppressor activity and effects of supernatants on other immunological assays are listed for CEM, 6T-CEM, 6T-CEM-20, and Az-CEM (an azaguanine-resistant CEM mutant) in the following Table 3:

TABLE 3

| | CEM | 6T-CEM | 6T-CEM-20 | Az-CEM |
|---|---|---|---|---|
| Aminopterin Sensitivity[1] | 98 | 10 | 2 | 3 |
| Doubling Time[2] | 20 | 24 | 20 | 26 |
| Karyotype[3] | 45 ± 16 | 72 ± 12 | 74 ± 14 | 70 ± 18 |
| T-Cell[4] Suppressor Activity | $5 \times 10^{-3}$ | $10^{-6}$ | $>10^{-6}$ | $<10^{-1}$ |
| B-Cell Suppressor Activity | $<10^{-1}$ | $<10^{-1}$ | $10^{-1}$ | $<10^{-1}$ |
| MLC[5] Suppressor Activity | $5 \times 10^{-3}$ | $5 \times 10^{-5}$ | $10^{-6}$ | $<10^{-1}$ |
| Effect on[6] the Generation of Cytotoxic T-Cells | 2 | 2 | 4 | 2 |

[1]% viability of the cells after 7 days exposure to 0.05 μg/ml of aminopterin.
[2]Time required for the cells to double the number from a starting concentration of $5 \times 10^5$ cells/ml.
[3]Chromosomes from 100 cells were counted, means and standard deviations were shown.
[4]Suppressor activity on T-Cell and B-Cell proliferation was measured according to the method described in Example IV of my EPO 127,394. The entry "$<10^{-1}$" means that lower than $10^{-1}$ dilution is required to attain 50% suppression of B cell proliferation. The entry ">$10^{-6}$" means that 50% suppression was attained at dilutions higher than $10^{-6}$.
[5]Suppressor activity on allogenic MLC was measured according to the method described in Example V of EPO 127,394. Dilutions of supernatant showing 50% suppression were shown. The entry "$<10^{-1}$" means that less than $10^{-1}$ dilution is required to attain 50% suppression of MLC reaction.
[6]Effect on the generation of cytotoxic T cells was measured according to the method described in Example VII of my EPO 127,394. Differences in % cytotoxicity between supernatant (used at $10^{-1}$ dilution) treated cells and medium treatedcells were shown.

B. Production of suppressive supernatants

6T-CEM cells were routinely maintained in α-MEM containing 10% FCS. For production of the suppressive supernatants from 6T-CEM, cells were washed and suspended at $2 \times 10^5$ cells/ml or $10^6$ cells/ml in α-MEM with 2% FCS. Supernatant was harvested 48 hours later and the functional activities were assessed.

C. Ammonium sulfate precipitation

Cell-free supernatant was centrifuged at 10,000 rpm for 20 minutes to remove any debris. Ammonium sulfate was then added gradually to give a final 50% ammonium sulfate saturation. After stirring for 45 minutes, the solution was centrifuged at 10,000 rpm for 30 minutes. The precipitate, which contained the suppressor activity, was exhaustively dialyzed against PBS. All steps were carried out in the cold and the pH was maintained between pH 7.0 and pH 7.4. This fraction of SAF was used in the Examples below.

D. Chromatography on Sephacryl S-200 column

The 50% ammonium sulfate fraction containing the suppressor activity was further purified on a Sephacryl S-200 superfine column (2.5 cm × 50 cm). The column was equilibrated with PBS and had a flow rate of 30 ml per hour. 2 ml of the dialyzed, 50% ammonium sulfate precipitated fraction was applied on the column. Elution was carried out with PBS and 5 ml volumes were collected. The protein profile was obtained by reading optical density at 280 nm.

In treating autoimmune disease, individual batches of SAF may be standardized by determining the highest dilution of SAF giving 80% suppression of Con A induced T lymphocyte proliferation in a 2-day assay. The reciprocal of such dilution is defined as the 'unit of activity' of SAF tested. (For instance, a batch which suppresses at $4 \times 10^{-5}$ dilution contains $2.5 \times 10^4$ units/ml). The absolute amount of SAF required for a particular treatment will depend on the duration and severity of the symptoms. In general, SAF may be given daily at a dose range of $2-10 \times 10^4$ units or 1–20 mg per kg of body weight until remission. SAF may be purified by gel filtration and ionic exchange chromatography or by SDS polyacrylamide electrophoresis until a single band is obtained. The specific activity of SAF should be approximately 0.5 to $2 \times 10^4$ units/mg. SAF may be administered in intravenous solution and it may be stored at −20° C. in vials that meet specifications for use as containers for injectables. The recommended preservatives are methyl and propyl parabens.

EXAMPLE 1 a. Introduction

Induction of autoimmune responses by injection of high concentrates of autologous or highly cross-reacting allogenic or xenogeneic tissue or organs has been used for the induction of autoimmune diseases such as autohemolytic anemia, autoimmune thyroiditis and autoimmune encephalomyelitis. Symptoms observed subsequently in the experimental animals suggest that these induced diseases closely mimic the human clinical diseases autoimmune hemolytic anemia, thyroiditis and multiple sclerosis, see H. S. Flad in *Proc. Soc. Exp. Biol. Med.* 131:121 (1969); A. D. Vladertine in *Science* 174:1137 (1971); and D. L. Gasser et al, in *Science* 181:873 (1973).

Autoimmune hemolytic anemia in humans is a classical autoimmune disease wherein autoantibodies to the patient's erythrocytes cause hemolysis and resulting anemia, see R. S. Evans et al. in *Ann. N.Y. Acad. Sci.* 124:422 (1965). One method of inducing erythrocyte autoantibodies experimentally in animals is to immunize mice with cross-reacting rat erythrocytes, see C. Y. Lau et al. in the Journal of *Immunology Vol.* 125, No. 4 pages 1634–1638 (1980). The duration of autoantibodies is self-limiting in most normal mouse strains and is probably controlled by a specific population of suppressor T cells, see J. H. L. Playfair et al. in *Nature (New Biology)* 243:213 (1973) and A. Cooke et al. in *Clin. Exp. Immunol.* 27:538 (1977). The extent of suppression varies from strain to strain. C57BL/6 mice apparently have a strong suppressor system and only very transient autoantibodies develop after immunization. However, in CBA and C3H, mice, erythrocyte autoantibodies can be detected by the DAIT for as long as 10 weeks after immunization, see A. Cooke, in *Nature* 273:154 (1978). On the other hand, N2B mice, the classic mouse model for human autoimmune hemolytic anemia, not only showed hyper-responsiveness to the induction, but, the erythrocyte autoantibody, once elicited, persisted until the death of the animals. Similarly, in the case of the SJL strain, which had been shown to be highly susceptible to the induction of experimental allogenic encephalomyelitis when subjected to induction, also failed to regulate autoantibody production through the loss of antigen-specific suppressor cells. Thus, failure to develop self-tolerance probably accounts for the disease manifestation, suggesting that experimental autoimmune hemolytic anemia is a good model for the in vivo investigation of experimental compounds.

The effect of SAF in suppressing or accelerating the decline of autoantibody titres to self-RBC was studied in C3H/J mice, a normal mouse strain which responds in this experimental model. It was found that SAF—in a dose-related manner—accelerated the decline of autoantibodies titres in this mouse model.

b. Procedure

Animals used:

Mice: Female C3H/J mice were obtained from Jackson Laboratories, Bar Harbor, Me. 10 mice were used per group. Rats: Female Long Evans rats were obtained from Charles River Laboraties, Mass.

Immunization:

Rat erythrocytes were collected from Long Evans rats, washed 3× and then injected i.p. at a cell concentration of $2 \times 10^8$ cells/mouse. After 2 weekly injections, mice were bled and the autoantibody titre tested. Mice were then divided into groups of 10 such that each group average autoantibody titre was similar. Mice were given one more immunization one week later.

SAF Treatment:

The 50% ammonium sulfate precipitated fraction of SAF, which had been dialyzed exhaustively against Hanks buffer containing 20% glycerol, was used. Control vehicles were either Hanks buffer with 20% glycerol or the 50% ammonium sulfate precipitated fraction of growth medium prepared in exactly the same way as SAF. SAF treatment was initiated on the same day as the last RBC immunization. Intraperitoneal SAF treatment were administered in 0.2 ml doses 5 times per week.

Antiserum:

Polyspecific rabbit anti-mouse immunoglobulin was obtained from Cedarlane Laboratories Ltd. Hornby, Ont. The antiserum was reconstituted with 2 ml of distilled water, aliquoted and frozen. A 1:64 dilution of this antiserum was used for the DAIT. The diluent used in the DAIT was PBS with 1% albumin.

Testing

A Student-t test was used to compare the autoantibody titre between the test group and the control group.

DAIT:

The presence of erythrocyte autoantibody was detected by a modified Coombs' test in microliter plates. Fifty microliters of blood were obtained weekly by tail bleeding. The mouse red cells were washed 4× with PBS and resuspended to a final concentration of 0.6%. Serial 2-fold dilutions of rabbit anti-mouse immunoglobulin (Cedarlane) were carried out in V-bottom microtitre wells with 1% albumin PBS as the diluent; 50 microliters of washed mouse cells were added to each well and the plates were mixed by a Vortex vibrator and sealed to avoid evaporation. The plates were left overnight at room temperature and read the next day. The titre of rabbit anti-mouse immunoglobulin was recorded as a measure of autoantibody bound to the red cells. Sharp and reproducible end points were obtained by using this microtitre method. Fifty microliters of blood from each animal was sufficient for the test. Results obtained from this method were directly comparable to results obtained by conventional Coombs' tests in tubes.

d. Results

In the DAIT test, the results were obtained as shown in Table 4:

TABLE 4

| Week # | AIHA $(Log_2)^+$ (Treatment in Week #1) | | |
|---|---|---|---|
| | Control | SAF (¼ Dilution) | SAF (⅛ Dilution) |
| 1 | 2.3 ± 2.7 | 2.4 ± 2.6 | 2.7 ± 2.9 |
| 2 | 6.5 ± 1.0 | 7.0 ± 1.4 | 7.5 ± 1.2 |
| 3 | 8.1 ± 1.1 | 7.3 ± 1.2 | 8.4 ± 0.8 |
| 4. | 7.4 ± 1.3 | 6.0 ± 0.9 | 6.0 ± 7.1 |
| 5 | 7.7 ± 1.3 | 6.5 ± 0.9 | 7.1 ± 1.1 |
| 6 | 7.4 ± 9.2 | 6.3 ± 0.9 | 6.6 ± 0.4 |
| 7 | 7.8 ± 1.0 | 5.8 ± 1.2 | 6.1 ± 1.0 |
| 8 | 8.5 ± 1.2 | 7.1 ± 0.9 | 7.8 ± 1.8 |
| 9 | 11.7 ± 3.8 | 8.4 ± 1.3* | 9.2 ± 1.9 |
| 10 | 9.7 ± 0.8 | 8.3 ± 1.4* | 8.2 ± 1.7 |
| 11 | 10.3 ± 1.9 | 7.5 ± 1.1* | 8.8 ± 1.4 |
| 12 | 5.9 ± 0.7 | 4.3 ± 0.8* | 5.0 ± 1.1* |
| 13 | 13.0 ± 3.3 | 8.6 ± 4.2* | 11.1 ± 3.2 |
| 14 | 8.4 ± 5.8 | 4.7 ± 3.8* | 7.7 ± 4.9 |

+Reported as highest titre (lowest concentration) of anti-serum giving an agglutination reaction of mouse red cells
*$p \leq 0.05$ For the first 8 weeks, SAF treated C3H/J mice developed autoantibody levels comparable to the control group. However, starting with week 9, differences between control and test groups began to emerge. Groups treated with SAF at ¼ and ⅛ dilutions showed longer autoantibody titres than the control group. The autoantibody titres declined much more rapidly in the SAF treated groups during the subsequent weeks and did so in a dose related manner. Groups treated with ¼ dilution of SAF showed a statistically significant decline in autoantibody titre, as compared to the control group from week 9 onwards. Groups treated with lower doses of SAF (⅛ and 1/16 dilutions) also showed lower titres of autoantibody production than the controls; however, the difference was not always statistically significant.

EXAMPLE 2

The procedures and testing of Example 1 were repeated with the exception that rat agglutinin titre measurements were also made.

i. In the DAIT, the results obtained are shown in Table 5:

TABLE 5

| Week # | AIHA (Log$_2$)+ | | | |
|---|---|---|---|---|
| | Control | SAF ¼ Dil. | SAF ⅛ Dil. | SAF 1/16 Dil. |
| 1 | 4.3 ± 1.3 | 4.7 ± 0.8 | 4.7 ± 0.8 | 4.9 ± 1.1 |
| 2 | 9.1 ± 1.5 | 9.1 ± 0.7 | 10.4 ± 3.3 | 9.2 ± 1.5 |
| 3 | 8.2 ± 0.9 | 7.8 ± 2.1 | 9.5 ± 0.7 | 8.6 ± 1.1 |
| 4 | 9.5 ± 0.5 | 8.2 ± 0.9 | 10.3 ± 1.7 | 9.4 ± 1.1 |
| 5 | 12.6 ± 1.4 | 11.8 ± 1.4 | 12.7 ± 2.8 | 12.1 ± 1.5 |
| 6 | 10.6 ± 1.0 | 9.4 ± 2.0 | 11.7 ± 3.0 | 10.4 ± 1.1 |
| 7 | 10.0 ± 0.9 | 9.2 ± 2.6 | 9.8 ± 1.8 | 8.5 ± 2.4 |
| 8 | 12.2 ± 1.5 | 10.4 ± 1.9 | 11.8 ± 2.1 | 10.7 ± 1.4 |
| 9 | 12.2 ± 1.4 | 10.1 ± 2.6* | 11.6 ± 1.6 | 9.6 ± 3.9 |
| 10 | 11.4 ± 2.2 | 9.4 + 1.8* | 10.3 ± 2.3 | 10.1 ± 3.1 |
| 11 | 12.0 ± 2.4 | 7.0 ± 4.2* | 7.8 ± 4.2 | 8.7 ± 5.1 |
| 12 | 11.8 ± 2.0 | 5.8 ± 3.0* | 8.1 ± 3.4 | 8.0 ± 4.1 |
| 13 | 10.0 ± 5.7 | 5.7 ± 3.9* | 9.3 ± 2.8 | 8.4 ± 4.6 |
| 14 | 10.8 ± 4.7 | 1.2 ± 2.5* | 4.7 ± 5.6* | 6.0 ± 5.2 |

*p ≤ 0.05
+Reported as the highest titre of antiserum giving agglutination of mouse red cells ii. Rat Agglutinin Titre Measurement:

The purpose of this measurement was to detect changes in the production of antibodies to foreign antigens caused by SAF. Serial 2-fold dilutions of the test sera were carried out in V bottom microtitre plates. Fifty microliters of 0.6% rat erythrocytes were added to each well. The agglutination titre was expressed as the last well giving agglutination.

The production of antibodies to the immunogen, rat erythrocytes, was monitored at weeks, 0, 3, 6, 9 and 12; results are shown in Table 6 below:

TABLE 6

| | Rat Agglutinin Titre | | | | |
|---|---|---|---|---|---|
| | Weeks | | | | |
| Groups | 0 | 3 | 6 | 9 | 12 |
| Control | 10.9 ± 0.8 | 14.4 ± 1.7 | 12.5 ± 1.0 | 14.3 ± 2.5 | 12.7 ± 1.5 |
| SAF ¼** | 10.8 ± 1.0 | 12.3 ± 0.8* | 10.7 ± 0.9* | 10.8 ± 1.2* | 10.0 ± 1.2* |
| SAF ⅛** | 10.4 ± 0.5 | 13.2 ± 1.5 | 11.8 ± 1.2 | 11.6 ± 0.9 | 12.8 ± 1.8 |
| SAF 1/16** | 10.2 ± 1.0 | 13.3 ± 1.9 | 12.0 ± 1.1 | 11.5 ± 1.9 | 11.3 ± 1.8 |

*p < 0.05
**dilution of SAF

Small but significant differences were observed between the control and high dose groups (¼ dilution at 5× injections) starting from week 3 onwards. Groups treated with lower doses of SAF did not show significant differences from the control group.

Examples 1 and 2 show that intraperitoneal injection of SAF 5×/week significantly suppressed the production of autoantibody. Thus, SAF treatment accelerated the process of suppression of an autoimmune response, a phenomena exhibited by normal mouse strains. The production of antibody to the immunogen, rat erythrocytes, was also reduced by optimal doses of SAF (as shown by rat agglutinin tests). The difference, though statistically significant, was small, suggesting that SAF suppressed antibody production to self antigens much more than it did to foreign antigens, suggesting a therapeutic role in autoimmune disease due to its selectivity.

It has been suggested by cell transfer experiments that suppression of autoantibody production in normal mouse strains is mediated by antigen specific suppressor cells. Whether SAF, which suppressed autoantibody production much more readily than antibody directed to foreign antigens was stimulating a population of antigen-specific suppressor cells is unclear. It is clear, however, that SAF reduced autoantibody production and is thus useful in the treatment of autoimmune diseases.

The cell line 6-T CEM and its subclone 6-T CEM-20 were deposited at the American Type Culture Collection, 12301 Parklawn Drive, Rockville, MD 20852 on Apr. 26, 1983 and were givenATCC accession No. CRL 8296 and CRL 8295, respectively.

What is claimed is:

1. A method for the treatment of a systemic or organ-specific autoimmune disease in a human in need of such treatment which comprises parenterally administering to the human an amount of a factor sufficient to alleviate the severity of the symptoms of said disease wherein said factor:
   (i) is secreted by a stable 6-thioquanine-resistant mutant of the lymphoblastoid cell line CEM,
   (ii) is non-mitogenic,
   (iii) is non-cytotoxic, and
   (ix) exhibits a greater suppressive effect on autoantibody production than on antibody to rat erythrocyte foreign antigens in a mouse immunized with said foreign antigens.

2. The method of claim 1, wherein said autoimmune disease is a systemic autoimmune disease.

3. The method of claim 2, wherein said autoimmune disease is Goodpasture's syndrome.

4. The method of claim 2, wherein said autoimmune disease is rheumatoid arthritis.

5. The method of claim 2, wherein said autoimmune disease is Sjogren's syndrome.

6. The method of claim 2, wherein said autoimmune disease is systemic lupus erythematosus.

7. The method of claim 1, wherein said autoimmune disease is an organ-specific autoimmune disease.

8. The method of claim 7, wherein said autoimmune disease is myasthenia gravis, autoimmune thyroiditis, autoimmune hemolytic anemia, autoimmune encephalomyelitis or mulitple sclerosis.

9. The method of claim 8, wherein said autoimmune disease is autoimmune hemolytic anemia.

10. The method of claim 8, wherein said autoimmune disease is multiple sclerosis.

11. The method of claim 1, wherein said parenteral administration is carried out intravenously.

12. The method of claim 1, wherein said mammal is a human.

13. The method of claim 1, wherein said cell line has a Karyotype of 72±12.

14. The method of claim 1, wherein said cell line has the properties of ATCC CRL 8295 or ATCC CRL 8296.

15. The method of claim 1, wherein said factor further:
   (iv) suppresses at least 90% of mitogen-induced T cell proliferation at a dilution of $10^{-6}$ but does not suppress mitogen-induced B cell proliferation at said dilution.

16. The method of claim 1, wherein said factor further:

(v) is contained in a high molecular weight protein of about 110,000 dalton.

17. The method of claim 1, wherein said factor further:
   (vi) exhibits maximum suppressor activity at physiological pH.

18. The method of claim 1, wherein said factor further:
   (vii) is inactivated at 56° C.

19. The method of claim 1, wherein said factor further:
   (viii) suppresses mouse spleen cell proliferation to mitogenic stimulation with the same potency as it suppresses human peripheral blood lymhocyte proliferation to mitogenic stimulation.

20. The method of claim 1, wherein said factor further:
   (iv) suppresses at least 90% of mitogen-induced T cell proliferation at a dilution of $10^{-6}$ but does not suppress mitogen-induced B cell proliferation at said dilution;
   (v) is contained in a high molecular weight protein of about 110,000 dalton;
   (vi) exhibits maximum suppressor activity at physiological pH;
   (vii) is inactivated at 56° C.; and
   (viii) suppresses mouse spleen cell proliferation to mitogenic stimulation with the same potency as it suppresses human peripheral blood lymphocyte proliferation to mitogenic stimulation.

* * * * *